(12) United States Patent
Bass (10) Patent No.: US 11,832,954 B2
(45) Date of Patent: *Dec. 5, 2023

(54) SENSORY-MOTOR GENERATION OF THERAPEUTIC MUSICAL TRACKS

(71) Applicant: Center for Music Therapy, Austin, TX (US)

(72) Inventor: Hope Bass, Austin, TX (US)

(73) Assignee: Biomedical Music Solutions, Inc., Austin, TX (US)

( * ) Notice: Subject to any disclaimer, the term of this patent is extended or adjusted under 35 U.S.C. 154(b) by 148 days.

This patent is subject to a terminal disclaimer.

(21) Appl. No.: 17/487,243

(22) Filed: Sep. 28, 2021

(65) Prior Publication Data

US 2022/0007996 A1 Jan. 13, 2022

Related U.S. Application Data

(63) Continuation of application No. 16/080,173, filed as application No. PCT/US2017/019876 on Feb. 28, 2017, now Pat. No. 11,160,490.

(60) Provisional application No. 62/420,179, filed on Nov. 10, 2016, provisional application No. 62/359,946, filed on Jul. 8, 2016, provisional application No. 62/300,849, filed on Feb. 28, 2016.

(51) Int. Cl.
*A61B 5/00* (2006.01)
*A63B 71/06* (2006.01)
*G16H 20/70* (2018.01)
*A61B 5/11* (2006.01)
*G10H 1/00* (2006.01)
*G16H 40/63* (2018.01)

(52) U.S. Cl.
CPC ............ *A61B 5/4088* (2013.01); *A61B 5/11* (2013.01); *A61B 5/4082* (2013.01); *A61B 5/4836* (2013.01); *G10H 1/0008* (2013.01); *G16H 20/70* (2018.01); *G16H 40/63* (2018.01)

(58) Field of Classification Search
CPC ......... A61B 5/0205; A61B 5/11; A61B 5/165; A61B 5/4082; A61B 5/4088; A61B 5/4836; A61B 5/681; A61B 5/7275; A61B 5/7405; G06F 16/00; G10H 1/0008; G16H 20/70
See application file for complete search history.

(56) References Cited

U.S. PATENT DOCUMENTS 11,160,490 B2 * 11/2021 Bass .................. G16H 20/70

* cited by examiner

Primary Examiner — Jon Eric C Morales
(74) Attorney, Agent, or Firm — The Culbertson Group, PC; Nathan H. Calvert (57) ABSTRACT

A patient therapy method and program product are provided for communicating with a patient monitor to obtain data from a patient engaged in physical therapy. A library of musical features includes a plurality of coordinated musical tracks associated with respective functional therapeutic outcomes. The functional therapeutic outcomes include gait characteristics comprising at least at strike, cadence, stride length deviations. Based on a selected functional therapeutic outcome, musical tracks are selected and mixed together at a desired tempo. The tracks are adjusted based on changes in patient data.

20 Claims, 2 Drawing Sheets

Audio Therapy Stream Generator Model

SENSORY-MOTOR GENERATION OF THERAPEUTIC MUSICAL TRACKS

CROSS-REFERENCE TO RELATED APPLICATIONS

This application is a Continuation of U.S. patent application Ser. No. 16/080,173 filed Aug. 27, 2018, and entitled "SENSORY-MOTOR GENERATION OF THERAPEUTIC MUSICAL TRACKS", which application is a national phase application of PCT Patent Application No. PCT/US2017/019876, filed Feb. 28, 2017, which application claims the benefit of U.S. provisional application No. 62/300,849 filed Feb. 28, 2016, 62/359,946, filed Jul. 8, 2016, and 62/420,179, filed Nov. 10, 2016, which applications are incorporated herein by reference.

BACKGROUND

I. Field of the Invention

The present invention relates generally to the fields of devices and methods for rhythmic therapy.

II. Description of Related Art

Music/rhythmic therapy has been used effectively to facilitate improvements in walking and other motor skills in patients with a variety of disorders including cerebral palsy and Parkinson's disease. However, such therapy is predominantly limited to a one on one interaction between the therapist and patient.

SUMMARY

Principles of the present disclosure provide a system for providing patient specific, audio stream to facilitate patient rehabilitation comprising a patient monitor in communication with a first computer, said first computer comprising a first computing apparatus having at least one microprocessor, display and memory storing instructions configured to instruct the at least one microprocessor to perform operations, the first computing apparatus comprising a receiver configured to obtain information from said patient monitor, software configured to monitor data obtained from said patient monitor and display output corresponding to said obtained data on said display, a library of musical features comprising recordings of plurality of coordinated musical tracks from a plurality of instruments or voices, and audio output, wherein the output of each of said tracks is independently controlled.

In some embodiments principles of the present disclosure provide a method for providing patient specific rehabilitation comprising engaging a patient in a rehabilitation exercise, wherein at least one characteristic of said patient is monitored, tracking the monitored characteristic from said monitor with a first computing apparatus having at least one microprocessor, display and memory storing instructions configured to instruct the at least one microprocessor to perform operations, the first computing apparatus comprising a receiver configured to obtain information from said patient monitor, and software configured to monitor data obtained from said patient monitor and display output corresponding to said obtained data on said display. The method further comprises audibly playing a first track from a library of musical features comprising a recordings of plurality of coordinated musical tracks from a plurality of instruments or voices, monitoring data from said monitor, audibly playing a second track simultaneously with said first track, wherein said first and second tracks are synchronized, monitoring data from said monitor and adjusting the tracks based on the change in data observed from said patient.

Principles of the present disclosure provide devices and methods for musical and/or rhythmic therapy. The method comprises identifying a patient in need of such therapy, identifying a motor defect of said patient and providing to said patient a musical track designed to facilitate therapy of the motor defect of said patient.

In some embodiment the system and methods include providing a system that receives input regarding a patient, input obtained from a sensor, input regarding a music catalog and functional information related to said music. The system provides for interpreting sensor data in combination with the client profile, considers prior treatment history as needed, identified appropriate beats per minute based on information received from said sensor and related to said patient, selecting at least one mix of musical selections of appropriate beats per minute and assembling an audio output stream.

In some embodiments the audio output stream finds use in playback for gait training or may be exported into a format for later listening by the user/patient.

Accordingly, the disclosure provides for a method of generating personalized training music tracks comprising inputting into a system patient information, sensor information and data related to musical tracks in a music library, compiling user information and sensor information to generate a personalized user score, identifying music tracks by the music tracks data applicable to the user score, and generating a playlist personalized for the patient. In some embodiments the music on the playlist is used for therapy under the care and/or supervision of a physician or therapist. In some embodiments the music is used by the patient without supervision.

In some embodiments, therefore, the disclosure provides a method of treating a patient in need thereof by providing personalized music tracks generated by methods described above and having the patient perform exercises or therapy while listening to said music. In some embodiments the patient performs exercised under the care and/or supervision of a physician or therapist. In some embodiments the music is used by the patient without supervision In addition, the method comprises receiving input from a device that has measured at least one characteristic of motor movement of a patient, identifying a motor defect of said patient based on said input, providing a musical track designed to facilitate therapy of the motor defect of said patient and integrating said musical track into said device.

It is contemplated that any embodiment of a method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

Rhythmic Auditory Stimulus (RAS) is a brain based music treatment created when you match the beat of the music with the correct speed that a person walks naturally. Without being bound by theory, RAS works because music coordinates the brain with a person's muscles. The brain anticipates the beat in the music it is hearing therefore communicating a smoother more efficient muscle pattern to the legs when walking. The longer you train to the music, the more a person's brain and muscles entrain to and internalize this beat. Therapists change the tempo of the music in increases of 5%-10% throughout the course of treatment until they reach the patient's individual goals for walking. When done with treatment the person's brain will reset its internal timing and control of their walking movements. A person is then able to walk at this tempo without the music better than prior to treatment.

When musical tracks designed to facilitate therapy for a particular motor deficit are combined with a medical device such as a FitBit, elliptical trainer, treadmill, bicycle (mobile or stationary), synergistic improvements in therapy are enabled.

Accordingly, in some embodiment the present disclosure provides systems and methods for treating or providing rehabilitation of patients in need thereof. The methods include surprising and unexpected improvements in Rhythmic Auditory Stimulation (RAS) and Patterned Sensory Enhancement (PSE) to catalyze more efficient motor coordination and control to improve overall gait, including balance, of person's effected by a movement impairment caused by injury, disease or a disorder.

In two decades of research using rhythmic/auditory cueing and synchronization strategies with movement, the use of RAS and a metronome have been shown to make improvements in the gait parameters of people with Parkinson's disease. Research also shows significant improvements using PSE, or live music interventions, which melodically, rhythmically, and tonally correlate with the functional patterns of the desired movement outcomes, PSE uses a musical component to impact the temporal and spatial parameters, similar to RAS, along with force patterns. Its main advantage over RAS is that, in addition to the rhythmic patterns stimulating movements, the pitch patterns simulate a change in spatial positions and the harmonic and dynamic patterns simulate applications of force and muscle tone. They have become available tools in the treatment of gait dysfunction by music therapist, physical therapists, nurses, doctors and other health professionals for their patients. Despite its proven success, little to no advancements have been made over the past two decades to improve or further the effectiveness of music protocols, technology's or tools used by physical therapists and other health professionals when RAS or PSE is deemed appropriate to enhance treatment outcomes.

While music is appreciated as providing a benefit for people including sick people or people who are otherwise considered patients, prior to the present disclosure there were not systems that provided for personalization of music therapy tracks. However, in view of the principles of the disclosure provided herein, musical tracks may be selected and provided to physicians/technicians/therapists and/or patients, wherein the music has been prepared based on the patient's characteristics, including ailment and treatment history, and sensor information, for in stance, received from a treadmill or FitBit sensor, and the like. Accordingly, principles of the present disclosure provide systems and devices utilizing a variety of musical attributes in a therapeutic or rehabilitative setting. Because of the developments in understanding the musical attributes that contribute to particular movements of a patient predictive, precise and personalized therapy or rehabilitation is achieved.

This new music design integrates music technologies using a new process in music recording and play back that are specifically designed so that PSE can be controlled and manipulated by the health professionals through a computerized system. This will allow health professionals to more specifically use the audio drivers for the motor system by customizing the sensory input through the Sensory Optimization Auditory Rehabilitation (SOAR) strategy in order to create predictable and precise gait parameter improvements during treatment sessions.

Accordingly, in some embodiments principles of the present disclosure provide for a method of improving performance in a patient or subject in need thereof. The method includes monitoring physiological parameters from the subject. The monitoring may be from a variety of inputs as described herein, including but not limited to FitBit, heart rate monitors, EKG, EMG, and machines, such as treadmills, bicycles, including mobile or stationary bicycles, and the like. The system provides for tailoring musical composition to the user, subject or patient by modifying a musical characteristic such as pace, pitch, tone, increasing scales, decreasing scales, increasing the number and/or complexity of the musical instruments, and/or increasing or decreasing the complexity of the harmonic structure or melody. In some embodiments the composition may be arranged to provide a lifting or declining sound which in turn is translated into an alteration in the physiological response of the patient.

As described herein, in some embodiments musical structure relates to and impacts non-musical functional movement of a person. The data describing the musical structure may be annotated and stored in a database of annotated musical tracks. In some embodiments, the musical score correlates with and reflects music notation to functional movement it is written to support. In some embodiments the musical pattern stands alone as musical structure to support one or more movement variables it was specifically written and coded for as well as work as whole musical composition as interlaying (locking) multiple music patterns/movement variables play simultaneously. For instance, certain musical structure correlates with changes in right heel strike, left heel strike, right knee bend, left knee bend, right arm swing, left arm swing and other body movements. In some embodiments musical pattern is clearly scored and coded in audio mix templates for the specific movement for which it was written including such information in audio file templates such as the range of steps per minute/beats per minute (SPM/BPM), the composition range that each can hold its musical integrity, the left ear, right ear, audio correlates, etc. Should capture sound as full band-width as technologically possible to create as live music experience in sound as possible.

In some embodiments software integrates audio file information with non-musical functional coding. Creation of music pairing (sensorimotor) movement algorithm that can deliver a prescribed audio file instantly to a user once movement diagnostics sensors/software has given movement diagnostics information to the music pairing (sensorimotor) movement algorithm.

A delivery system has capacity for full band width audio files, and has left/right capacity (i.e. headphones, left/right speakers (channels).

Principles of the present disclosure provide a device and method that combine medical devise with music. This includes the composition, recording and technical integration of music tracks into medical devices used to improve the rehabilitation patients with motor defects such as those with Parkinson's Disease and children with Cerebral Palsy.

Rehabilitation takes the form of many activities including but not limited to walking, dancing, running, using an elliptical trainer, treadmill, mobile bicycle, stationary bicycle, weights, and the like.

In some embodiments the medical device records data from the patient including name, height, weight, age, gender, date of birth, heart rate, blood pressure, strength, stride, step length and/or step speed, diagnosis and the like. In other embodiments the patient information is provided to a system for storage and analysis. In addition, other information, such as but not limited to sensor information is provided to the system for storage and analysis. By sensor information is meant any information obtained from or related to a patient physical or mental attribute, such as EKG, treadmill data, FitBit sensor data, and the like.

Accordingly, principles of the present disclosure provide a system for providing patient specific audio stream to facilitate patient rehabilitation. In one embodiment, the system comprises a monitor in communication with a first computer or computing apparatus, the first computing apparatus having at least one microprocessor, display and memory storing instructions configured to instruct a microprocessor to perform operations. The computing apparatus in some embodiments contains a receiver configured to obtain information from a monitor. In addition, the system comprises software configured to monitor data obtained from the monitor and display output corresponding to the obtain data on the display. In some embodiments, the monitor detects patient characteristics including heart rate, respiration, strength, cadence, balance, weight shift, body rotation, arm swinging or walking pattern. In some embodiments, the monitor and receiver are in wireless or in some embodiments wired communication. In some embodiments, data obtained from the monitor is viewed on a display and can be viewed by a therapist, by the patient, or by a third-party at a plurality of monitors if needed.

In some embodiments, the monitor may be worn by the patient. For instance, the monitor may be a heart rate monitor, FitBit, EKG, smart watch, such as but not limited to an iWatch, and the like. In some embodiments, the monitor may be found in a piece of exercise equipment or associated with the piece of exercise equipment. Non-limiting examples of exercise equipment that find use herein include but are not limited to a treadmill, elliptical trainer, stationary bicycle, mobile bicycle, rowing machine, weight machine and the like.

Whether worn on the patient or in connection with exercise equipment, monitors made take a variety of characteristics about the patient, including heart rate, respiration, strength, heel strike, gait stride symmetry, velocity, cadence, balance, weight shift, body rotation, arm swinging, normalized walking pattern and the like.

In some embodiments the medical device records data from the patient including height, weight, heart rate, blood pressure, strength, stride, velocity, step length, symmetry and/or step speed, and the like are input into the system and used in the generation of tracks.

As described herein, input from data sources comes from existing software and devices. The system described herein serves as a bridge for software in devices that gather sensory data such gait information, kinematics, along with important end users information regarding their music preferences, age, height, weight, gender, diagnosis, name, as well as have a preexisting catalog of music in formats such as DSD or its equivalent which is encoded with the corresponding sensorimotor functional data as a key code for the audio therapy stream generator to synchronize with.

In some embodiments the system records a user's therapy session and musical choice/prescription. This may be observed as a time stamped audio files and data stored in the Client Treatment History. In some embodiments the system provides the option to record and/or then upload a file, such as an MP3 file, for end users to independently use at later time on audio compatible devices. In some embodiments the system allows for manual adjustment from therapist observation to adjust audio therapy stream generator. Adjustments include but are not limited to the ability to control around 5%-10% only increases in tempo and to integrate sensory data and sync the data with prescribed therapy protocol.

The system as described herein also comprises a library of musical features. This library comprises recordings having a plurality of coordinated musical tracks from a plurality of instruments or voices. By coordinated musical tracks is meant musical tracks associated with a particular song, or a given therapeutic outcome. For instance, one track may contain music played by a drum for a particular song while a second track may contain music played by a trombone for the same song. Alternatively, one track may contain music played by a drum for the purpose of evoking a particular therapeutic effect such as heel strike on a patient, while the second track may contain music played by a trombone for evoking the same or different therapeutic effect, such as knee bend or lift.

Accordingly, the library comprises a plurality of tracks from a plurality of instruments or voices for each song In some embodiments the library comprises a plurality of tracks from a plurality of instruments or voices to evoke particular physical or emotional responses of a patient. As is appreciated by one of skill in the art, the number of instruments can be large and accordingly so can the number of tracks. In some embodiments, the number of tracks for each song is around 2, 3, 4, 5, 6, 7, 8, 9, 10, 15, 20, or 25 tracks In some embodiments the same instruments is used to record multiple tracks or voice is used in multiple tracks. In some embodiments the same song or tracks for a particular song or track to evoke a particular response of a patient are recorded at different tempo ranges to fit movement needs within these ranges. It has been found that recordings at slow tempos find use in facilitating rehabilitation of more challenged patients and that as the patient improves tracks recorded at faster tempos can be used. Persons with severe injury or impairment to the brain move at tempo ranges 0-40 beats per minute, which is considered a profound movement impairment. Therefore compositions following this methodology must be composed and recorded at these tempo ranges to facilitate patients movement needs to support their progress throughout rehabilitation process up to fullest possible recovery. Therefore a full tempo range from 0-150+ bpm/spm must be provided in the musical library and be accessible via devices and corresponding algorithm. In some embodiments the compositions are around 0-200 bpm, from 1-190 bpm, from 2-150 bpm, from 5-120 bpm. In some embodiments the bpm are less than 100 bpm, less than 50 bpm, less than 40 bpm, less than 30 bpm, less than 20 bpm, less than 10 bpm. In some embodiments the bpm is from 1-40 bpm, from 2-35 bpm, from 5-30 bpm.

As described herein, patients having disorders as described herein respond to music, sounds, and rhythms in different ways. Principles of the present disclosure therefore provide for the use of certain sounds or composition structures to effect different mechanical movements of a patient. In some embodiments musical attributes that can be modified and have therapeutic or rehabilitative benefits for a patient include, but are not limited to tempo, meter, force, as well as sensory patterns through tonal, harmonic structures, and directional movements, including but not limited to: e.g. side to side—for patient to shift their weight from left foot to right foot the volume is increased or decreased with accent put into music to emphasize the shift to the right foot side stronger than the left or visa versa depending on the patients functional needs, up/down-musical sensory patterns corresponding to a leg, knee or arm lifting upward or downward; the knee example would be facilitated by correlating a functional knee bend with a corresponding bending trombone pitch patterned to played with increasing volume as patient brings knee higher with stronger force until their knee reaches targeted height before trombone bends pitch downward with decreasing force and volume to end movement with full downward completed correct step cycle, swing; arm or leg forward with, backward, upward, downward motion, the functional movement pattern would be sensory enhanced and facilitated by corresponding a violin using forward to backward bowing motion with simulates arm swing in longer pulled bowing for longer fuller, smoother swing of arm or play short bowing motion for shorter, quicker swing, drop; of heel in spatial time with beat sensory correlates with drum played on downbeat of 4/4 time to match normalized walking cadence, high/low how high or how low an arm or leg should swing, or upward, forward pulling long sustained notes, upward harmonic progressions or floating upward tones and musical phrases coincide with postural alignment and facilitate patient to hold trunk upright and head up higher, long, short, notes coincide with what the stride length should be and can coincide with patterns such as a bass line. Exemplary relationships between motor challenges and musical/rhythmic techniques, to facilitate directed therapy or rehabilitation are provided in Table 1.

| Gait Issues | Composition Structures to Address Issues | Instrumentation and Compositional Possibilities |
|---|---|---|
| Initiation of Movement | (RAS) Beat/Tempo set at pace of patients intrinsic gait | Drum: Bass kick. Kick to Snare or Tom combo. Walking bass line (Upright Bass, Xylophone, Chromatic Instruments, Etc.) |
| Control of Movement | (RAS) Beat/Tempo set at pace of patients intrinsic gait. With (PSE) supporting variations in movement. | Rhythmic, Chromatic Instruments, paired with instruments that can bend sound, create circular, upward-downward, pulling, sliding, sounds. (Horns, Violin, Harp, etc.) |
| Heel Strike | (RAS) Beat/Tempo set at pace of patients intrinsic gait | Drums: Pitched Timpani, Xylophone |
| Heel/Toe Roll | (RAS) Beat/Tempo set at pace of patients intrinsic gait, with (PSE) and/or sung verbal cue/track to facilitate foiling sound. | Chromatic Instruments, or instruments that can bend sound, create circular, upward, downward, pulling, sliding, sounds. (Horns, Violin, Harp, etc.) |
| Right Knee Bend | (PSE) pulling upward and drop down, sound like knee bend Over (RAS) beat track. | Instruments that can bend sound, create circular, upward, downward, pulling, sliding, sounds. (Horns, Violin. Harp, etc.) |
| Left Knee Bend | (PSE) pulling upward and drop down, sound like knee bend Over (RAS) beat track. | Instruments that can bend sound, create circular, upward, downward, pulling, sliding, sounds (Horns, Violin, Harp, etc.) |
| Hip Flexion | (PSE) Sway/Bend, forward back, sound Over (RAS) beat track. | Chromatic Instruments, Violin, Texturing percussion like Cabasa, logo, latin type sounds, Guiro |
| Hip Rotation | (PSE) Twist, swing, sound Over (RAS) beat track. | Chromatic Instruments, Violin, Texturing percussion like Cabasa, Togo, latin type sounds, Guiro |
| Weight Shift | (PSE) Side to side sound partern. Over (RAS) beat track. | Swaying, Chordal, pitch movement, with upward to downward melody line, etc. Bowed instruments, violin, etc. |
| Upper Body Rotation | (PSE) Twist, swing, sound. Over (RAS) beat track. | Chromatic Instruments, Texturing percussion like Cabasa. Togo, latin type sounds, Guiro. Or Jazz Swing, structures. |
| Arm Swing | (PSE) Swing, sound Over (RAS) beat track. | Chromatic Instruments. Texturing percussion like Cabasa, Togo, latin type sounds. Guiro. Or Jazz Swing, structures. |
| Muscle Hypertonic (tight, contracted) | Chordal, sustained/suspended, tonal structures with arpeggiated patterns and DE-emphasized beat. Rhythmic structure still there but chordal tonal pattern cues muscle movement | Celtic drone, dulcimer type sounds, Strings, Harp, Piano, Xylophone, still keeping rhythm but moving in sustained, fluid, connected ways. Fluid feel with distinct tonal release as well as rhythmic. |
| Muscle Hypotonic (no tone, reactive) | Down and up beat usually needed, in complementary pattern. | Chromatic instruments important. Steady, even, simple, predictable, controlled forward, walking pattern to sound. Tic/Toc, Wood Blocks, Violin, Vibes |
| Stride Length Deviations | (RAS) Beat with (PSE) option to emphasize (Right Leg or Left Leg) deviation | Use of accents and texturing of instruments, (i.e. pulled bass note instead of staccato of other leg, Dynamics can he used on one stride vs. the other. On Violin Bowed, Plucked sound. |

| Gait Issues | Composition Structures to Address Issues | Instrumentation and Compositional Possibilities |
| --- | --- | --- |
| Gait Velocity | (RAS) 5%-10% Tempo increase or decrease one entrainment is taking place. | Software with composition ranges of each track built into it that can make upward and downward temporal moves. But not exceed compositions tempo range. |

In some embodiments, personalized music tracks or musical scores can be generated using the system described herein. While in the presence of a professional such as a therapist, nurse, physician and the like, manual adjustments of tracks can be performed. For instance, while a patient is performing rehabilitation, a first track is audibly played and then the patient's characteristics monitored. A second track is then audibly played and the patient's response monitored. If the second track did not negatively affect the patient, a third track may be added. As needed, tracks may be added and turned off and this need not necessarily be performed in consecutive order. For instance, tracks one, two, three and four may be added in consecutive order but when removing tracks, there is no need to remove them in the order or even reverse order that they were added.

In some embodiments, the tracks may be added and adjusted by using the software in the system. In this automated system, once the data is input into the system, an Audio Therapy Stream Generator is used to generate personalized audio tracks for patient therapy. Audio Therapy Stream Generators are used for the pervasive integration of clinically supported/prescribed music protocol with existing and future biomedical equipment, devices and software technologies used in clinical and non-clinical environments. By Audio Therapy Stream Generators is meant a system that compiles input including, but not limited to pertinent patient profile data, sensor data, music catalog (including, but not limited too, encoded functional data: i.e. sensorimotor, respiratory, heart rate correlates), and an ongoing/real time, client audio stream treatment history catalog. In some embodiments data is obtained from a client electronic medical record (EMR) and in some embodiments, data or records from a therapeutic or rehabilitative sessions are submitted to the client EMR. Notably, in providing the data to the EMR the system allows for a client's/patient's support/care team ecosystem to stay apprised of the client's/patient's activity or activities and results thereof.

These inputs are interpreted and combined to select, mix and match with music composition stems and functional desired outcomes (i.e. sensorimotor, NICU oxygen saturation levels, cardio/pulmonary, pain/analgesia, stress/anxiety, mood states, cognition/speech). The algorithm (generator) then assembles and plays back a prescribed audio therapy stream. In some embodiments metadata is coded into the tracks. The metadata may include, but is not limited to information defining the musical sensory pattern(s), features and design per targeted functional needs and desired outcomes. The stream is observable and controllable by clinicians, if when necessary, to be manually adjusted to desired clinical parameters or with an automatic shut off of musical stream when sensor data inputs indicate patient is not responding within functional outcomes ranges preset within formulas. The Audio Therapy Stream is recordable to any format, such as but not limited to MP3, format for independent client use at a later time. It may be used within stationary and ambulatory clinical and non-clinical settings in both wearable and detached device form.

In some embodiments principles for composition of sensorimotor audio tracks (compositions) comprise musical structure should relate to a non-musical functional movement. For instance, the musical score correlates and reflects music notation to functional movement it is written to support; musical pattern stands alone as musical structure to support movement variable it was specifically written and coded for as well as work as whole musical composition as interlaying (locking) multiple music patterns/movement variables play simultaneously. (i e. R Heel Strike, L Heel Strike, R Knee Bend, L Knee Bend, Right Arm Swing, Left Arm Swing, etc.); musical pattern is clearly scored and coded in audio mix templates for the specific movement for which it was written, including such information in the audio file templates such as the range of SPM/BPM, the composition range that each can hold its musical integrity, the left ear, right ear, audio correlates, etc. should capture sound as full band-width as technologically possible to create as live music experience in sound as possible; software should integrate audio file information with non-musical functional coding. The system therefore provides for a creation of music pairing (sensorimotor) movement algorithm that can deliver prescribed audio file instantly to user once movement diagnostics sensors/software has given movement diagnostics information to the music pairing (sensorimotor) movement algorithm; delivery system should have capacity for full band width audio files, must have left/right capacity (i.e. headphones, left/right speakers (channels).

Once prepared the music tracks can be used in therapy for other medical defects, NICU (PAL) pacifier assisted lullaby, cardio pulmonary therapy, pain/audio analgesia, stress/anxiety, mood states, cognitive/speech functions and the like.

Principles of the present disclosure provide a device and method that combines medical device with music. This includes the composition, recording and technical integration of music tracks into medical devices used to improve the walking of patients with motor defects such as those with Parkinson's Disease and children with Cerebral Palsy.

Non-limiting examples of disorders that find use in the systems and methods described herein include but are not limited to cerebral palsy, Parkinson's Disease, brain injury, stroke, cancer, multiple sclerosis, Huntington's Disease, autism, PDD Pervasive Developmental Delays, sensory processing disorders, second and third degree burns, amputation, medically fragile: adults, children, and infants, heart disease, COPD, premature infants, aneurysm, heart attack, chronic pain, mood disorders, depression, anxiety disorders, and bi-polar, immune deficiency patients, Alzheimer's Disease, dementia, intellectually disabled, Down Syndrome, childbirth, failure to thrive infants and children, post traumatic stress disorder, encephalopathy, Crohn's Disease, AIDS, Fragile X Syndrome, Lewy Body Disease, fibromyalgia, sleep disorders, apnea, and/or stress related disorders.

Figure 1:
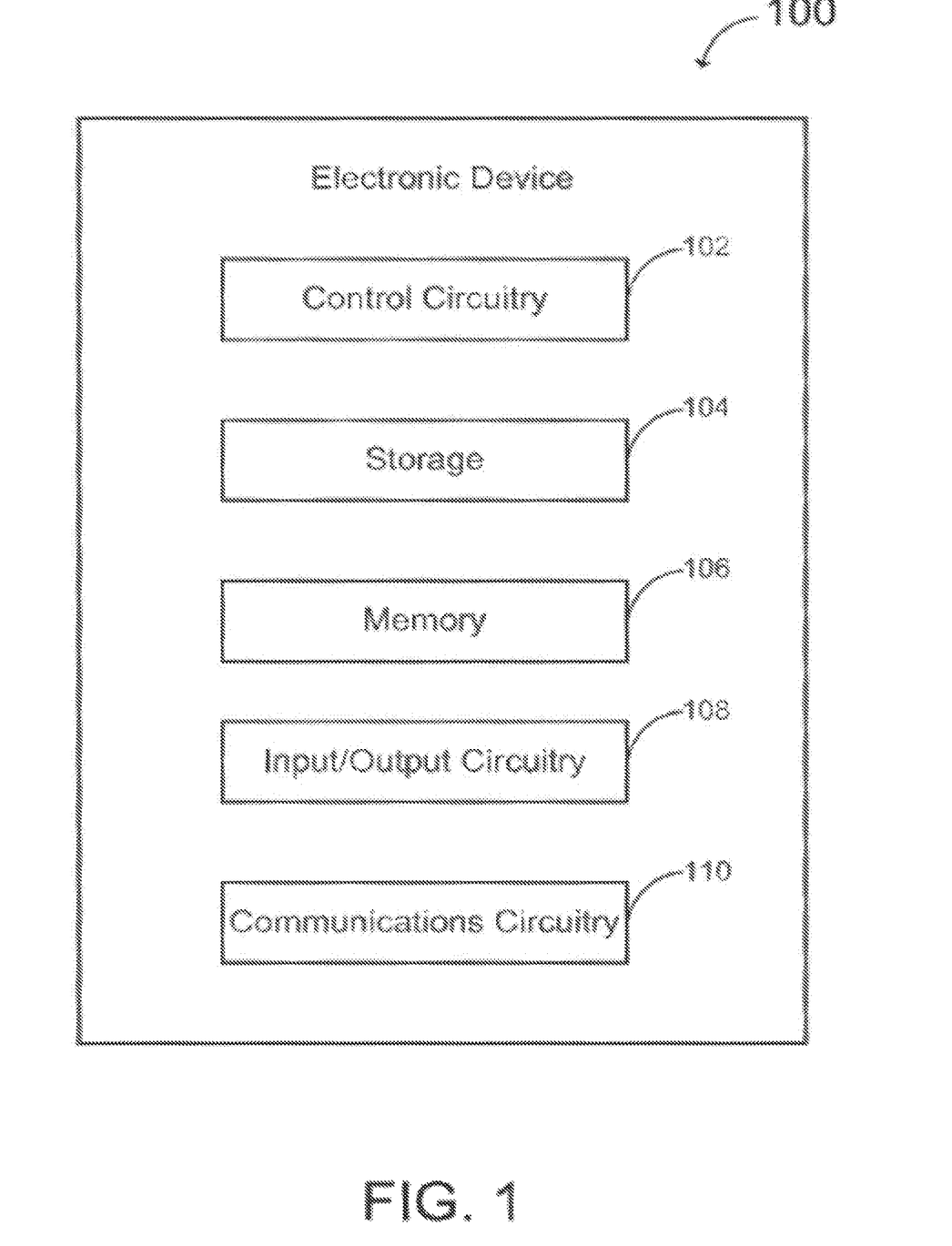
FIG. 1 is a block diagram of an illustrative electronic device for developing personalized, therapeutic music in accordance with some embodiments of the invention.
Figure 2:
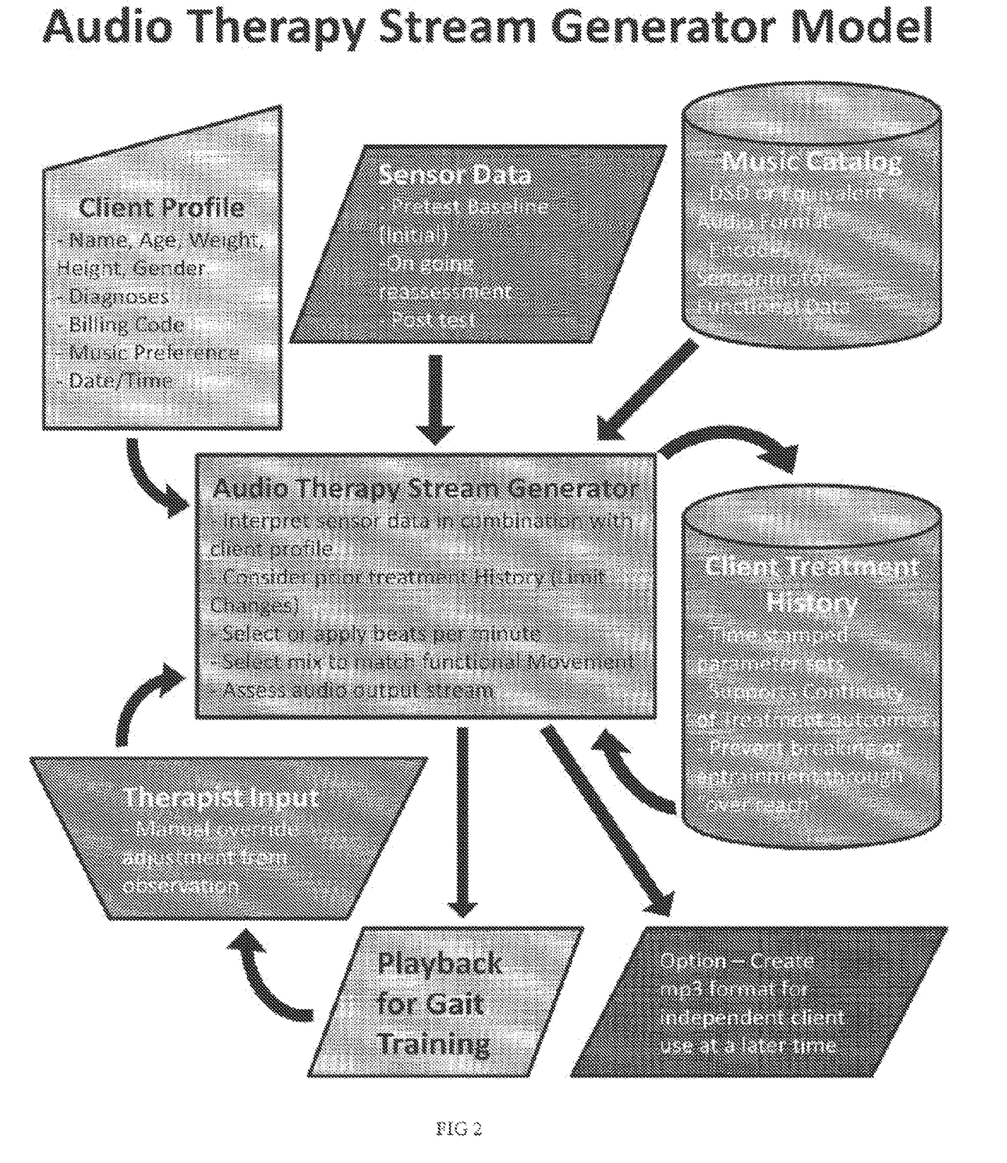
FIG. 2 is a flow chart describing data that is input into the system described herein as well as possible outcomes and uses of the personalized musical tracks.

FIG. 1 is a block diagram of an illustrative but not limiting electronic device for providing a system operative for generating personalized, therapeutic music programs or selections for a patient in need thereof in accordance with some embodiments of the invention.

Electronic device 100 can include control circuitry 102, storage 104, memory 106, input/output ("I/O") circuitry 108, and communications circuitry 110. In some embodiments, one or more of the components of electronic device 100 can be combined or omitted (e.g., storage 104 and memory 106 may be combined). In some embodiments, electronic device 100 can include other components not combined or included in those shown in FIG. 1 (e.g., recording devices, health monitors, activity sensors, sensors motion detection components, a power supply such as a battery or kinetics, a display, bus, a positioning system, a camera, an input mechanism, etc.), or several instances of the components shown in FIG. 1. For the sake of simplicity, only one of each of the components is shown in FIG. 1.

Electronic device 100 can include any suitable type of electronic device. For example, electronic device 100 can include a portable electronic device that the user may hold in his or her hand, such as a smartphone (e.g., an iPhone made available by Apple Inc. of Cupertino, Calif. or an Android device such as those produced and sold by Samsung). As another example, electronic device 100 can include a larger portable electronic device, such as a tablet or laptop computer. As yet another example, electronic device 100 can include a substantially fixed electronic device, such as a desktop computer.

Control circuitry 102 can include any processing circuitry or processor operative to control the operations and performance of electronic device 100. For example, control circuitry 102 can be used to run operating system applications, firmware applications, media playback applications, media editing applications, or any other application In some embodiments, control circuitry 102 can drive a display and process inputs received from a user interface.

Storage 104 can include, for example, one or more storage mediums including a hard-drive, solid state drive, flash memory, permanent memory such as ROM, any other suitable type of storage component, or any combination thereof. Storage 104 can store, for example, media data (e.g., music and video files), application data (e.g., for implementing functions on electronic device 100), firmware, user preference information data (e.g., media playback preferences), authentication information (e.g. libraries of data associated with authorized users), lifestyle information data (e.g., song preferences), exercise information data (e.g., information obtained by exercise monitoring equipment), transaction information data (e.g., information such as credit card information), wireless connection information data (e.g., information that can enable electronic device 100 to establish a wireless connection), subscription information data (e.g., information that keeps track of podcasts or television shows or other media a user subscribes to), contact information data (e.g., telephone numbers and email addresses), calendar information data, and any other suitable data or any combination thereof.

Memory 106 can include cache memory, semi-permanent memory such as RAM, and/or one or more different types of memory used for temporarily storing data In some embodiments, memory 106 can also be used for storing data used to operate electronic device applications, or any other type of data that can be stored in storage 104. In some embodiments, memory 106 and storage 104 can be combined as a single storage medium.

I/O circuitry 108 can be operative to convert (and encode/decode, if necessary) analog signals and other signals into digital data. In some embodiments, I/O circuitry 108 can also convert digital data into any other type of signal, and vice-versa. For example, I/O circuitry 108 can receive and convert physical contact inputs (e.g., from a multi-touch screen), physical movements (e.g., from a mouse or sensor), analog audio signals (e.g., from a microphone), or any other input. The digital data can be provided to and received from control circuitry 102, storage 104, memory 106, or any other component of electronic device 100. Although I/O circuitry 108 is illustrated in FIG. 1 as a single component of electronic device 100, several instances of I/O circuitry 108 can be included in electronic device 100.

Electronic device 100 can include any suitable interface or component for allowing a user to provide inputs to I/O circuitry 108. For example, electronic device 100 can include any suitable input mechanism, such as for example, a button, keypad, dial, a click wheel, or a touch screen In some embodiments, electronic device 100 can include a capacitive sensing mechanism, or a multi-touch capacitive sensing mechanism.

In some embodiments, electronic device 100 can include specialized output circuitry associated with output devices such as, for example, one or more audio outputs. The audio output can include one or more speakers (e.g., mono or stereo speakers) built into electronic device 100, or an audio component that is remotely coupled to electronic device 100 (e.g., a headset, headphones or ear buds that can be coupled to communications device with a wire or wirelessly).

In some embodiments, I/O circuitry 108 can include display circuitry (e.g., a screen or projection system) for providing a display visible to the user. For example, the display circuitry can include a screen (e.g., an LCD screen) that is incorporated in electronics device 100. As another example, the display circuitry can include a movable display or a projecting system for providing a display of content on a surface remote from electronic device 100 (e.g., a video projector). In some embodiments, the display circuitry can include a coder/decoder (CODEC) to convert digital media data into analog signals. For example, the display circuitry (or other appropriate circuitry within electronic device 100) can include video CODECs, audio CODECs, or any other suitable type of CODEC.

The display circuitry also can include display driver circuitry, circuitry for driving display drivers, or both. The display circuitry can be operative to display content (e.g., media playback information, application screens for applications implemented on the electronic device, information regarding ongoing communications operations, information regarding incoming communications requests, or device operation screens) under the direction of control circuitry 102. Alternatively, the display circuitry can be operative to provide instructions to a remote display.

Communications circuitry 110 can include any suitable communications circuitry operative to connect to a communications network and to transmit communications (e.g., voice or data) from electronic device 100 to other devices within the communications network. Communications circuitry 110 can be operative to interface with the communications network, using any suitable communications protocol such as, for example, Wi-Fi (e.g., a 802.11 protocol), Bluetooth, radio frequency systems (e.g., 900 MHz, 1.4 GHz, and 5.6 GHz communication systems), infrared, GSM, GSM plus EDGE, CDMA, LTE and other cellular protocols, VOIP, or any other suitable protocol.

In some embodiments, communications circuitry 110 can be operative to create a communications network using any suitable communications protocol. For example, communications circuitry 110 can create a short-range communications network using a short-range communications protocol to connect to other devices. For example, communications circuitry 110 can be operative to create a local communications network using the Bluetooth protocol to couple electronic device 100 with a Bluetooth headset.

Electronic device 100 can include one more instances of communications circuitry 110 for simultaneously performing several communications operations using different communications networks, although only one is shown in FIG.

1 to avoid overcomplicating the drawing. For example, electronic device 100 can include a first instance of communications circuitry 110 for communicating over a cellular network, and a second instance of communications circuitry 110 for communicating over Wi-Fi or using Bluetooth. In some embodiments, the same instance of communications circuity 110 can be operative to provide for communications over several communications networks.

In some embodiments, electronic device 100 can be coupled a host device for data transfers, synching the communications device, software or firmware updates, providing performance information to a remote source (e.g., providing riding characteristics to a remove server) or performing any other suitable operation that can require electronic device 100 to be coupled to a host device. Several electronic devices 100 can be coupled to a single host device using the host device as a server. Alternatively or additionally, electronic device 100 can be coupled to several host devices (e.g., for each of the plurality of the host devices to serve as a backup for data stored in electronic device 100).

EXAMPLES

Example 1

This new music design integrates music technologies using a new process in music recording and play back that are specifically designed so that PSE can be controlled and manipulated by the health professionals through a computerized system. This will allow health professionals to more specifically use the audio drivers for the motor system by customizing the sensory input through the SOAR strategy in order to create predictable and precise gait parameter improvements during treatment sessions.

Subjects: 5 people with Parkinson's disease: 4 male; 1 female. All subjects gave informed written consent.
Inclusion criteria:
a. Parkinson's disease
b. Hoehn & Yahr stage 1-3
c. Stable medication regimen
d. Able to walk for 30 minutes without assistance
e. Montreal Cognitive Assessment 26
Exclusion Criteria
a. Deep brain stimulator
b. Montreal Cognitive Assessment<26
c. Acute orthopedic injuries
d. Currently receiving physical or music therapy
e. Hearing impairment
Methods:
a. One Group Pretest—Posttest Design
b. Outcome measures
   MiniBESTest (Balance)
   10 meter walk test (Velocity)
   6 minute walk test
   Biodex gait assessment
Procedure:
Day 1: Pre-test and customize music setup
Day 1-7. Walk 20-30 minutes 2×/day listening to the music
Day 7: Reassessment and tempo increase
Day 7-14: Walk 20-30 minutes 2×/day listening to the music
Day 14: Reassessment and tempo increase
Day 14-21: Walk 20-30 minutes 2×/day listening to the music
After final walking session: Post-test Data Analysis:
Due to the one group pretest-posttest design having no control group for comparison, scores were compared along with Minimal Detectable Change in outcome measures.

Results

Outcome Measure Change

| | MiniBest | | CWS | | FWS | | 6 MWT | |
|---|---|---|---|---|---|---|---|---|
| Subj # | pre | post | pre | post | pre | post | pre | post |
| 1 | 27 | 27 | 1.59 | 1.61 | 1.83 | 2.22* | 1845 | 2032 |
| 2 | 20 | 26* | 1.3 | 1.27 | 1.83 | 1.74 | 1636 | 1634 |
| 3 | 25 | 28 | 1.43 | 1.45 | 1.68 | 1.86 | 1494 | 1456 |
| 4 | 5 | 21* | 0.77 | 1.11* | 0.87 | 1.35* | 998 | 1470* |
| 5 | 16 | 25 | 1.15 | 1.22 | 1.35 | 1.54 | 1358 | 1568 |

*Indicates MDC met
CWS—comfortable walking speed in meters/second,
FWS—fast walking speed in meters/second,
6 MWT—6 minute walking test in feet Biodex Measure Change

| | Left step length (cm) | | Right step length (cm) | |
|---|---|---|---|---|
| Subject # | pre | pest | pre | post |
| 1 | 49 | 58 | 48 | 57 |
| 2 | 36 | 40 | 40 | 42 |
| 3 | 49 | 50 | 46 | 48 |
| 4 | 32 | 39 | 32 | 38 |
| 5 | 23 | 26 | 22 | 28 |

Example 2

Sensory Optimized Auditory Rehabilitation (S.O.A.R.)

Individualized Fitting Process for Customized Music Tracks. Motor System

Process for fitting the music stems to functional movements:
First Fitting:
1. Start with heel strike (RAS), match stem tempo to baseline walking cadence.
2. Playback only the music stem which match patients heel strike, keep all other tracks off.
3. Allow the patient to walk to this for 60 seconds up to 3 mins.
4. Observe, watch for subtle entrainment. Music Therapists and/or Physical Therapist will decide next functional movement to fit.
5. Music Therapist will pick correct next matching stem to fit.
6. Playback heel/strike with next matching stem turned on and added in.
7. Allow patient to walk to this for 60 seconds up to 5 mins.
8. Observe, watch for subtle functional corrections or exacerbation of movement issues. Discontinue stem playback if exacerbation is observed. Return to step #5 until correct fit of musical stem is matched up to support/improve person's movement.

Second and all Follow Up Fittings:
1. Reassess heel strike and cadence (RAS). Confirm established and good entrainment has taken place, first without music, then with patients customized S.O.A.R. music program from prior fitting playing back while they are walking.
2. Playback music stems, moving the stems tempos 5-10% upward, while patient continues to walk.
3. Allow patient to walk to this for 60 seconds up to 3 mins.
4. Observe, watch for optimized entrainment at new tempo. Music Therapists and/or Physical Therapist will decide next functional movement needing to be fitted. In this second fitting PSE and other postural stability, gait symmetry, stems are layered into S.O.A.R. strategy's mix if they were not deemed appropriate in first fitting.
5. Music Therapist will pick correct next matching stems to fit.
6. Music Therapist will playback each stem, muting and unmuting stems per therapist judgment, based on therapists measurements and observation of patient walking during gait exercise.
7. Allow patient to walk to this for 60 seconds up to 5 mins to this stem strategy prior to mixing.
8. Observe, watch for subtle functional corrections or exacerbation of movement issues. Discontinue stem playback if exacerbation is observed. Return to step #5 until correct fit of musical stem is matched up to support/improve person's overall gait and movement.

The invention claimed is:

1. A method for providing patient specific rehabilitation comprising:
communicating with a patient monitor to obtain data from a patient engaged in physical therapy;
accessing a library of musical features comprising a plurality of coordinated musical tracks from a plurality of instruments or voices, including compositions each with multiple associated musical tracks and data associating each of the musical tracks to a respective one or more functional therapeutic outcomes, wherein the functional therapeutic outcomes include gait characteristics comprising at least heel strike, cadence, stride length deviations;
based on a first selected one of the functional therapeutic outcomes, selecting a first musical track from the library of musical features;
audibly playing the first musical track from the library of musical features to the patient while the patient is engaged in physical therapy;
monitoring data obtained from said patient monitor;
based on a second selected one of the functional therapeutic outcomes, accessing the library of musical features and selecting a second musical track having a tempo the same as that of the first musical track; and
audibly playing the second musical track simultaneously with said first musical track.

2. The method according to claim 1, further comprising adjusting the musical tracks, wherein said adjustment comprises adding or removing a musical track played simultaneously with the first musical track based on a change in one or more monitored characteristics associated with the data in response to addition of a musical track.

3. The method according to claim 2, wherein said adjustment comprises adding a third musical track played simultaneously with the first musical track when at least one of the one or more monitored characteristics demonstrates patient improvement in response to addition of the second musical track, and wherein the third musical track includes a different musical voice or instrument for the same song as the first musical track at the same tempo as the first musical track.

4. The method according to claim 2, wherein said adjustment comprises removing the second musical track when at least one of the one or more monitored characteristics demonstrates patient regression in response to addition of the second musical track.

5. The method according to claim 1 wherein said patient monitor detects patient characteristics comprising least heel strike, cadence, stride length deviations.

6. The method according to claim 1, further comprising displaying data from said patient monitor on a display to be seen by a service provider or said patient.

7. The method according to claim 1, wherein said patient monitor includes at least one sensor on a treadmill.

8. The method according to claim 1, further comprising changing the tempo of the first and second musical tracks, said changing associated with the patient changing a cadence of walking.

9. The method according to claim 8, wherein said patient monitor further comprises at least one sensor worn by said patient.

10. The method according to claim 1, further comprising automatically adding and removing musical tracks played simultaneously with the first musical track and synchronized with the first musical track based on the monitored data and patient response.

11. The method according to claim 1, wherein the library comprises recordings of compositions covering movement ranges from at least 5-150+ bpm/spm, and includes multiple tracks of different voices or instruments for the same song at the same tempo.

12. A tangible, non-transitory computer readable media holding a program product including instructions executable by at least one processor for:
communicating with a patient monitor to obtain data from a patient engaged in physical therapy;
accessing a library of musical features comprising recordings of a plurality of coordinated musical tracks from a plurality of instruments or voices, and data associating each of the musical tracks to a respective one or more functional therapeutic outcomes, wherein the functional therapeutic outcomes include gait characteristics comprising at least heel strike, cadence, stride length deviations;
based on a first selected one of the functional therapeutic outcomes, selecting a first musical track from the library of musical features,
audibly playing the first musical track from the library of musical features to the patient while the patient is engaged in physical therapy;
monitoring data obtained from said patient monitor;
based on a second selected one of the functional therapeutic outcomes, accessing the library of musical features and selecting a second musical track; and
audibly playing the second musical track simultaneously with said first musical track, wherein said first and second musical tracks are synchronized.

13. The media holding a program product of claim 12, wherein the program product is further executable for adjusting the musical tracks, wherein said adjustment comprises adding or removing a musical track played simultaneously with the first musical track based on a change in one or more monitored characteristics associated with the data in response to addition of a musical track.

14. The media holding a program product of claim 13, wherein said adjustment comprises adding a third musical track played simultaneously with the first musical track when at least one of the one or more monitored characteristics demonstrates patient improvement in response to addition of the second musical track, and wherein the third musical track includes a different musical voice or instrument for the same song as the first musical track at a similar tempo to the first musical track.

15. The media holding a program product of claim 13, wherein said adjustment comprises removing the second musical track when at least one of the one or more monitored characteristics demonstrates patient regression in response to addition of the second musical track.

16. The media holding a program product of claim 12, wherein said patient monitor detects patient characteristics comprising at least heel strike, cadence, stride length deviations.

17. The media holding a program product of claim 12, wherein said patient monitor includes at least one sensor on a treadmill.

18. The media holding a program product of claim 17, wherein the program product is further executable for changing a tempo of the first and second musical tracks, said changing associated with the patient changing a cadence of walking.

19. The media holding a program product of claim 12, wherein the program product is further executable for automatically adding and removing musical tracks played simultaneously with the first musical track and synchronized with the first musical track based on the monitored data and patient response.

20. The media holding a program product of claim 12, wherein the library comprises recordings of compositions covering movement ranges from at least 5-150+ bpm/spm, and includes multiple tracks of different voices or instruments for the same song at a similar tempo.

\* \* \* \* \*